United States Patent [19]
Petruzzi et al.

[11] Patent Number: 4,765,331
[45] Date of Patent: Aug. 23, 1988

[54] ELECTROSURGICAL DEVICE WITH TREATMENT ARC OF LESS THAN 360 DEGREES

[75] Inventors: Claude E. Petruzzi, Bronxville; Robert H. Quint, Jamaica, both of N.Y.; Frank D. D'Amelio, Naugatuck, Conn.; Dominick G. Esposito, Mamaroneck, N.Y.

[73] Assignee: Circon Corporation, Santa Barbara, Calif.

[21] Appl. No.: 13,246

[22] Filed: Feb. 10, 1987

[51] Int. Cl.[4] .............................................. A61B 17/36
[52] U.S. Cl. ........................ 128/303.14; 120/303.17
[58] Field of Search ... 128/4, 6, 303.1, 303.13–303.17, 128/755, 772

[56] References Cited

U.S. PATENT DOCUMENTS

| | | | |
|---|---|---|---|
| 164,184 | 6/1875 | Kidder | 128/784 |
| 659,409 | 10/1900 | Mosher | 128/303.11 |
| 932,775 | 8/1909 | Gaston | 128/303.11 |
| 1,366,756 | 1/1921 | Wappler | . |
| 1,814,791 | 7/1931 | Ende | . |
| 1,983,669 | 12/1934 | Kimble | . |
| 2,275,167 | 3/1942 | Bierman | . |
| 2,382,109 | 8/1945 | Sheiffele | 128/4 |
| 2,484,059 | 10/1949 | Wallace | 128/303.15 |
| 3,460,539 | 8/1969 | Anhalt, Sr. | 128/303 |
| 3,692,020 | 9/1972 | Schied | 128/755 |
| 3,854,473 | 12/1974 | Matsuo | 128/772 |
| 3,901,242 | 8/1975 | Storz | 128/303 |
| 3,902,949 | 9/1975 | Haberlen et al. | 128/275 |
| 3,920,021 | 11/1975 | Hiltebrandt | 128/303 |
| 3,974,833 | 8/1976 | Durden, III | 128/275 |
| 3,987,795 | 10/1976 | Morrison | 128/303 |
| 4,011,872 | 3/1977 | Komiya | 128/303 |
| 4,033,351 | 7/1977 | Hetzel | 128/303 |
| 4,161,950 | 7/1979 | Doss et al. | 128/303 |
| 4,202,337 | 5/1980 | Hren et al. | 128/303 |
| 4,228,800 | 10/1980 | Degler, Jr. et al. | 128/303 |
| 4,248,231 | 2/1981 | Herczog et al. | 128/303 |
| 4,271,829 | 6/1981 | Heckele | 128/6 |
| 4,532,924 | 8/1985 | Auth et al. | 128/303 |
| 4,554,929 | 11/1985 | Samson et al. | 128/772 |

FOREIGN PATENT DOCUMENTS

| | | | |
|---|---|---|---|
| 2222820 | 11/1973 | Fed. Rep. of Germany | . |
| 771920 | 10/1934 | France | . |
| 8503859 | 9/1985 | PCT Int'l Appl. | 128/303.17 |
| 401320 | 5/1978 | Sweden | . |
| 243478 | 7/1946 | Switzerland | . |
| 2037167 | 7/1980 | United Kingdom | . |
| 644491 | 1/1979 | U.S.S.R. | . |
| 0683726 | 9/1979 | U.S.S.R. | 128/755 |

OTHER PUBLICATIONS

"MBB-AT Proctology Infrared Coagulator" brochure.

*Primary Examiner*—Max Hindenburg
*Attorney, Agent, or Firm*—Perman & Green

[57] ABSTRACT

An electrosurgical device for use in the treatment of tissue, particularly in the esophageal and anal regions of the body. The device comprises a multipolar probe body sized for passage into and within a body cavity whose tissue is to be treated without the aid of an endoscope. The probe body includes an active member for providing focused treatment of tissue, the active member being cylindrical and having a peripheral surface on which are mounted a plurality of electrodes, those of one polarity being interposed with those of the opposite polarity. The length of the electrodes can be chosen to obtain desired longitudinal focussing. Additionally, the electrodes can be positioned within a restricted arc to obtain desired peripheral focussing. The probe body also includes non active rounded cap members at its proximal and distal ends, and at its proximal end is mounted on a shaft which extends to the user. A filiform may be mounted on the distal end of the probe body to aid in its insertion into the esophagus. A handle can be attached to the shaft to enable the user to easily adjust the longitudinal positioning of the probe body as well as rotate the probe body about its longitudinal axis to precisely focus on the tissue to be treated without adversely affecting surrounding tissue.

34 Claims, 8 Drawing Sheets

ELECTROSURGICAL DEVICE WITH TREATMENT ARC OF LESS THAN 360 DEGREES

BACKGROUND OF THE INVENTION

1. Field of the Invention

This invention relates generally to electrosurgery and, more specifically, to a multipolar electrosurgical device for use in precision surgery with the ability to more precisely focus the desired treatment.

2. Prior Art

The use of heat for the cauterization of bleeding wounds dates to ancient times. In the present century, the use of radio frequency (RF) electrical current traveling through a portion of the body has been widely used to stop bleeding. Cauterization of tissue arises by virtue of its resistivity to RF energy. In the cauterization of blood, the proteins in it are heated to a temperature at which the proteins congeal in a manner similar to the process involved in the cooking of egg white. RF energy is preferred because its frequency is above that which could otherwise cause neuro-muscular stimulation. Several modes of RF cauterization of tissue are employed, such as monopolar or bipolar coagulation.

In monopolar coagulation, an active electrode of small dimensions such as of the order of one to two millimeters is applied to the bleeding site and the current path is completed through the body to a distanced electrical return plate in contact with a large surface area of the body such as the buttocks. One technique in which the monopolar mode may be employed involves fulguration which is the use of a spark or arc from the active electrode to the tissue. In bipolar coagulation, the two active electrodes are closely spaced and are of the order of fractions of millimeters or larger so that the current path is confined to a local region of the tissue.

Another technique for stopping bleeding involves the delivery of thermal energy, such as from a resistively heated probe as described in an article entitled "The Heater Probe: A New Endoscopic Method For Stopping Massive Gastrointestinal Bleeding" by R. L. Protell appearing in Vol. 74, No. 2, Part 1, pages 257–262 of *Gastroentology*, 1978. Laser energy has been suggested as described in an article entitled "Treatment Technique For Massive Upper Gastrointestinal Bleeding: General Considerations" by R. Dwyer in Fleisher D., Hensen D., Bright-Asare P. Eds., *Therapeutic Laser Endoscopy In Gastrointestinal Disease*, Boston, Martinies Nijhof 1983, pp. 87–89.

A comparison of these various coagulating techniques appears at pages 362–366 of an article entitled "Endoscope Thermal Treatment of Upper G. I. Bleeding", by J. H. Johnson, *Endoscopy Review*, July, 1986, pp. 12–26. Thus, it is well known that tissue proteins coagulate at temperatures of 50°–100° C.

The coagulation of bleeding vessels such as in the case of bleeding ulcers in gastrointestinal parts of the body generally requires use of a long endoscope from the distal end of which the bleeding area first must be identified and subsequently treated with an instrument passed through a channel provided in the endoscope. Locating the bleeding site is not easy since often the tissue wall being investigated may be moving, debris in the form of particles is likely to be present and interfere with vision and the blood flow itself tends to obscure the bleeding sources. These sources can be very small, of the order of less than a millimeter across, with many present in a particular area and each to be coagulated.

The endoscope, or the device put through it, therefore, is also provided with a wash channel through which a fluid such as a liquid or gas can be supplied to flush away the debris and permit visual scrutiny of the tissue area to be treated. In the above identified Endoscope Laser Treatment article, a flow of gas which is coaxial with the laser fiber is used to clear tissue. In a known electrosurgical device of the bipolar type, a pair of conductors are embedded in the wall of a catheter whose central bore is used to supply gas or liquid to the tissue area to be treated. The conductors project in the form of spaced-apart loops from a distal end of the catheter.

When a tissue area is to be treated, each tiny source of blood is subjected to heat treatment. This means the clearing of tissue with a wash of fluid, followed by the application of heat, again clearing the area and applying heat and so on until all of the bleeding areas have been coagulated. In such treatment, the repeated applications should be made with facility in an accurate manner with a minimum of undesirable side effects such as the sticking of the coagulating device to tissue areas.

The laser technique has the advantage of not requiring physical contact, and thus avoiding such sticking problems, but because of the variable way in which different tissue conditions permit absorption of the laser energy, precise control during tissue treatment is difficult. The monopolar electrosurgical device tends to injure tissue not intended to be treated and even cause damage in the target area itself such as by excessively deep effects in the target area. Hence, bipolar electrosurgical treatment of tissue has been proposed and used to improve safety inasmuch as the electric current is confined to the small area between electrodes. Over the years, numerous bipolar devices have been devised.

For example, starting with an early 1875 U.S. Pat. No. 164,184 to Kidder, a bipolar electrosurgical device is proposed wherein a pair of conductors are spirally wound onto a rubber probe body in which the conductors are embedded. The conductors are shown terminated at a distal hemispherically shaped end of the probe body. A thermally heated knife is described and shown in the U.S. Pat. No. 1,366,756 to R. H. Wappler who employed a pair of half-round cross-sectionally shaped conductor rods twisted about an insulator to connect to a heater-knife. In 1934, Kimble proposed a bipolar electrosurgical device in U.S. Pat. No. 1,983,669 wherein a pair of conductors are shown twisted around a common insulator and project from a retainer body in a manner useful for side-wise or head-on applications to a tissue area.

The U.S. Pat. No. 4,011,872 to Komiya proposes an electrosurgical device wherein, for example, as shown in FIGS. 5, 9 and 11, one conductor is connected to a high frequency energy source and is formed of three or four electrodes. The electrodes individually extend from a distal end with spacings between electrodes being variable to accommodate or grasp differently sized tissue areas. In the U.S. Pat. No. 3,987,795 to Morrison, an electrosurgical device is described to operate in a mode which is intermediate the mono and bipolar modes of electrosurgery. This is achieved by mounting on one body, made of ceramic or glass, an active electrode and a return electrode whose surface area is made significantly larger than that of the active electrode. Various probe configurations are illustrated in the drawings.

Although these prior art electrosurgical devices are useful, they often do not provide satisfactory operation for a number of reasons. For instance, as previously noted, it is important that the probe body with which a cauterizing high frequency current is supplied can be repeatedly and precisely made to impinge upon the tiny blood vessel openings in the tissue area being treated independent of the orientation of the probe. This requires that as the probe is manually controlled at the proximal end of an endoscope, proper electrical contact is achieved to coagulate a blood vessel or other tissue target area whether the probe body is applied head-on, obliquely or side-wise to the tissue area.

Use of electrode configurations, as shown or described in the above prior art, thus frequently is unsatisfactory because of the larger number of probe applications needed to treat a tissue target or achieve coagulation of a bleeding tissue area.

The commonly assigned U.S. Pat. No. 4,532,924 to Auth et al discloses an improved electrosurgical device according to which a more consistent and accurate tissue treatment is obtained with a multipolar probe body on which at least one pair of conductors is distributed in a predetermined manner. As described with respect to one embodiment, the probe body is sized so that it can be passed through a channel of an endoscope from its proximal end. The probe body is provided with electrodes which are branched to form a plurality of electrode strips. The electrodes of different conductors are selectively sized and generally uniformly distributed in spaced apart pairs, over the distal end and side of the peripheral surface of the probe body. The ratio of the width of the electrodes to the spacing between them is so selected as to provide, with a predetermined minimum number of spaced apart pairs of electrodes, omnidirectional multipolar treatment of tissue when the probe body is operatively projected from the distal end of the endoscope.

The use of one or more pairs of electrodes of which may be branched to form a plurality of electrode strips assures at least bipolar or multiple bipolar tissue contact when the probe body is applied while the probe body is small enough to electrically coagulate the individual blood vessels from the distal end of an endoscope. A particularly effective probe body in accordance with the invention employs at least six electrode strips, from one or more pairs of electrodes, constituting the equivalent of six bipolar coagulating devices, around the peripheral surface of the endoscopically passable probe body. With such an electrosurgical device, two or more of the electrode strips can make tissue contact and such contact can be made independent of the orientation of the probe body for effective treatment of tissue such as gastric bleeding ulcers.

SUMMARY OF THE INVENTION

The present invention represents yet a further improvement over known bipolar electrosurgical devices. As technology has improved, it has become more and more desirable to better focus the heat on the specific tissue to be treated while leaving the surrounding tissue unaffected. The present invention achieves this goal by appropriately locating the electrodes on the probe body. An electrosurgical device embodying this construction is disclosed for use in the treatment of tissue, particularly in the esophageal, rectal and anal regions of the body although it is applicable to treat tissue in a wide range of other body locations, both internal and external.

Indeed, the invention described herein is particularly applicable to the treatment of cancerous tumors such as in the esophagus, rectal or anal areas. The device is also used for the treatment of hemmorhoids. In all of these applications the area to be treated is usually only a portion of the wall of the duct and thus the instrument has been designed so that the harm to healthy tissue adjacent to the cancerous area is minimized. In the esophageal area, one of the concerns is keeping the esophagus open as long as possible in the patient so that the patient can injest food. Sometimes the cancer grows to such a degree before treatment that it blocks off almost the entire esophagus. In these circumstances only a very thin diameter instrument can be used to treat the cancerous tissue at first. Care must be taken to contain treatment to just the cancerous tissue and to prevent the destruction of healthy tissue surrounding it. It is in instances of this nature that the construction of the invention enabling the focusing of the treatment of the tissue is of exceptional benefit.

Thus, the device comprises a bipolar probe body which may be utilized for the treatment of either external or internal body tissue. In the event the tissue to be treated is located internally, the device is sized for passage into and within a body cavity with or without the aid of an endoscope. The probe body includes an active member for providing focused treatment of tissue. The active member may be generally cylindrical shaped, barrel shaped, arcuate shape or any other functional shape and may have a peripheral surface on which are mounted a plurality of electrodes, those of one polarity being interposed with those of the opposite polarity. The length of the electrodes can be chosen to obtain desired longitudinal focusing, and they can also be positioned within a restricted arc to obtain desired peripheral focussing.

The electrodes may be branched into several electrode strips. The probe body also includes a non active rounded or contoured cap member at a first end, and at a second, opposite end, is mounted on a support shaft which extends to the user. A shape of the cap member may be any suitable one and may be provided at its second end in the event the probe body is of a different diameter from the support shaft to assure a smooth transition between the two members. A filliform may be mounted on the first end of the probe body to aid in its insertion into and movement through the esophagus. A handle for the user may be attached to the shaft such that the user can easily adjust the longitudinal positioning of the probe body as well as rotate the probe body about its longitudinal axis to precisely focus on the tissue to be treated without adversely affecting surrounding tissue.

The invention has been designed for the rapid and effective palliative treatment of esophageal, rectal and anal obstructions. It can be provided in a series of graduated probe sizes for use under fluoroscopy and/or direct vision and/or direct endoscopic vision. Tissue dessication occurs tangentially to create a patent lumen, enabling adequate passage of food or waste matter. A central irrigation channel through the device may be provided to allow for cleaning of the site throughout treatment.

Other and further features, objects, advantages, and benefits of the invention will become apparent from the following description taken in conjunction with the following drawings. It is to be understood that both the foregoing general description and the following detailed description are exemplary and explanatory but not restrictive of the invention. The accompanying drawings which are incorporated in, and constitute a part of the invention, illustrate different embodiments of the invention and, together with the description, serve to explain the principles of the invention in general terms. Like numerals refer to like parts throughout.

DETAILED DESCRIPTION OF THE DRAWINGS

Figure 19:
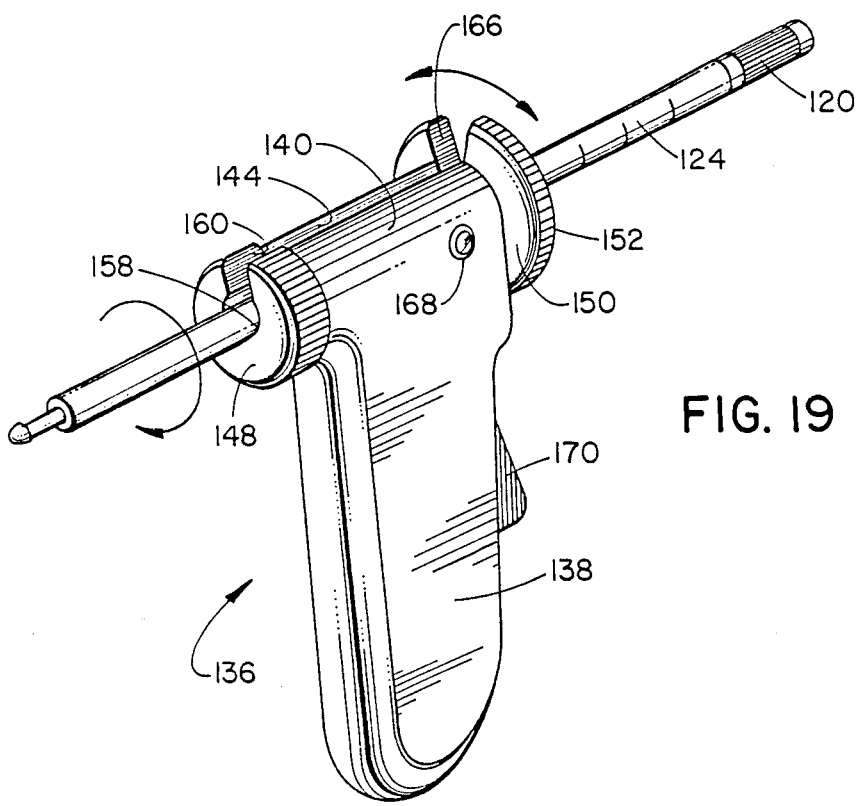
FIG. 19 is a perspective view of still another embodiment of the invention.
Figure 21:
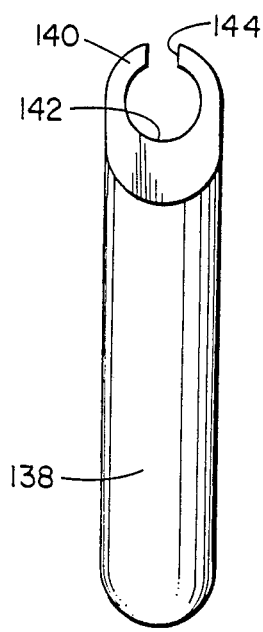
Figure 20:
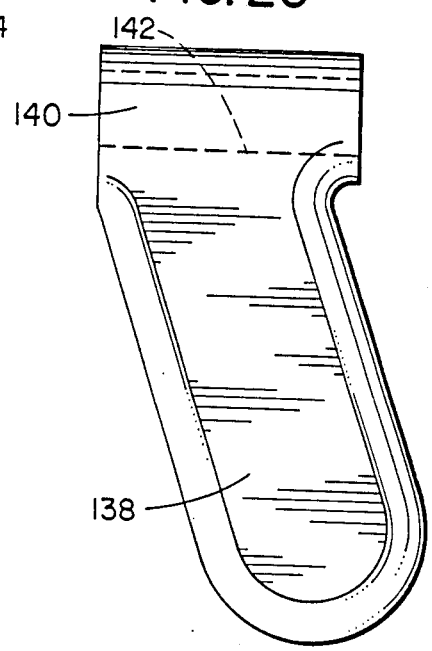
Figure 22:
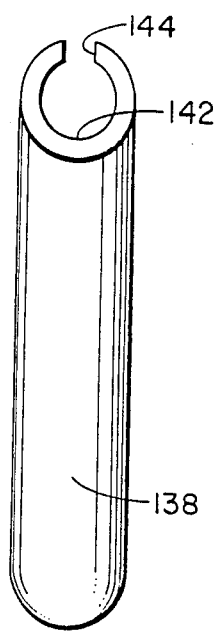
Figure 23:
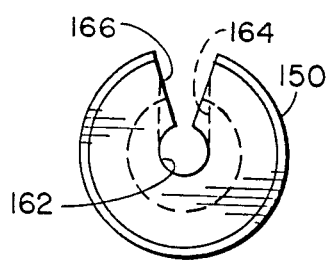
Figure 24:
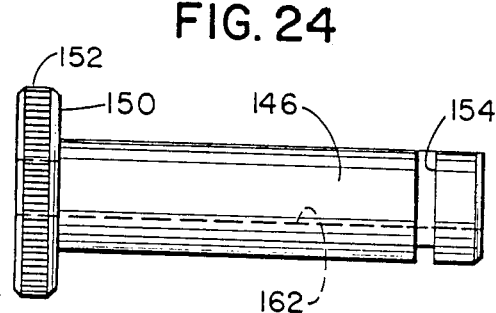
Figure 25:
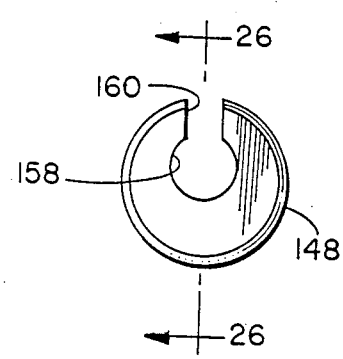
Figure 26:
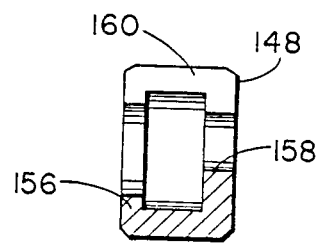

FIGS. 20, 21, and 22 are side elevation and opposite end elevation views, respectively, illustrating a portion of the embodiment depicted in FIG. 19;

FIG. 23 is an end elevation view of another component partially illustrated in FIG. 19;

FIG. 24 is a side elevation view of the component illustrated in FIG. 23;

FIG. 25 is an end elevation view of another component partially illustrated in FIG. 19; and FIG. 26 is a cross section view taken generally along line 26—26 in FIG. 25.

DETAILED DESCRIPTION OF THE PREFERRED EMBODIMENTS

Figure 1:
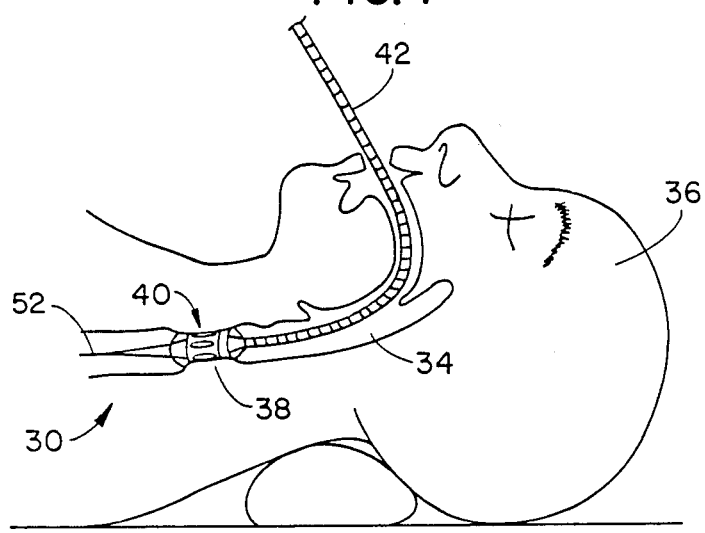
FIG. 1 is a diagrammatic representation illustrating the use of one embodiment of the invention.
Figure 2:
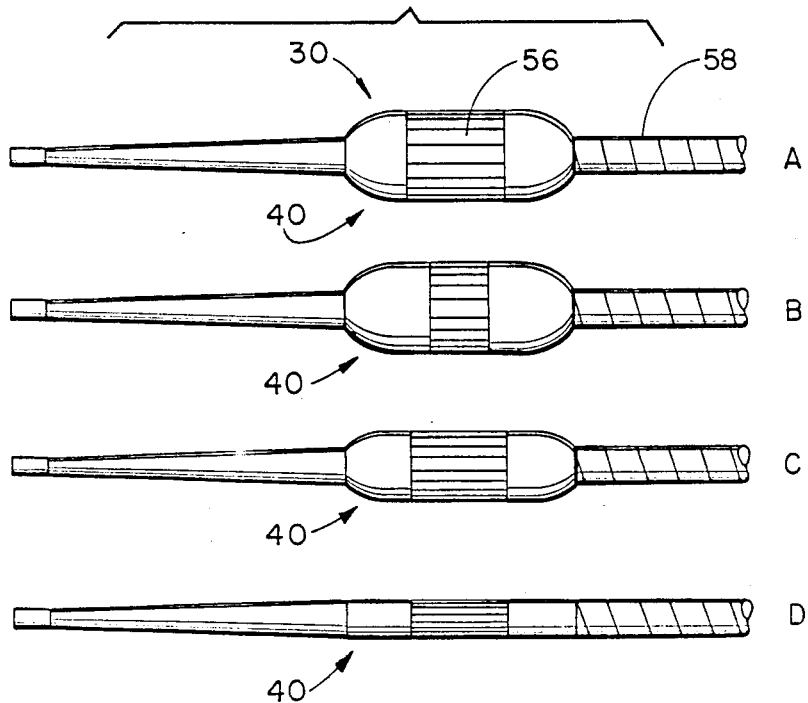
FIG. 2 are side elevation views, respectively, of four graduated sizes of the invention illustrated in FIG. 1.
Figure 3:
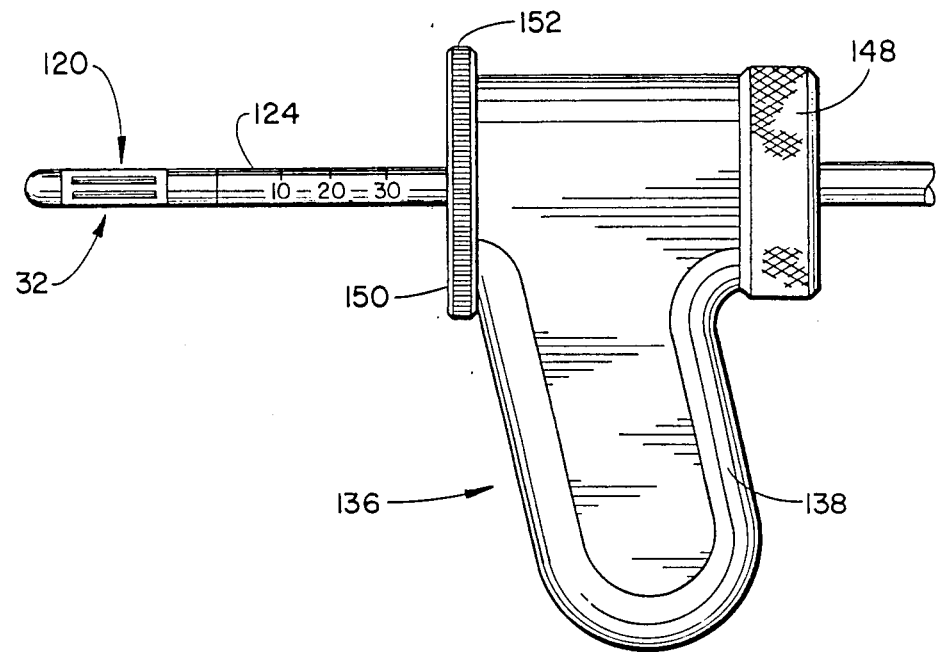
FIG. 3 is a side elevation view illustrating another embodiment of the invention.
Figure 4:
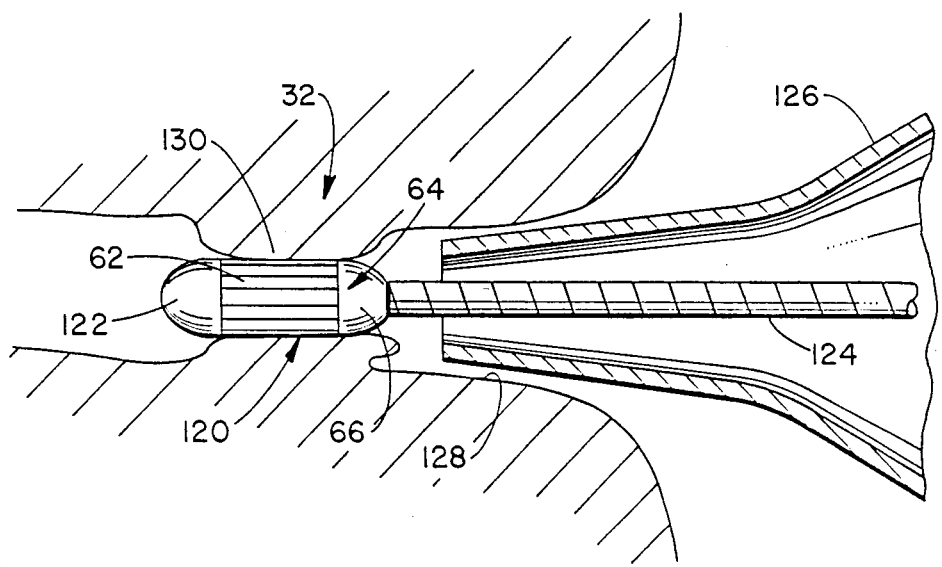
FIG. 4 is a detail side elevation view, certain parts being cut away and in section, illustrating a typical use of the embodiment of the invention illustrated in FIG. 3.

Turn now to the drawings and, initially to FIGS. 1-4 which are generally illustrative of an electrosurgical device having a probe for the use in the treatment of tissue in the human body. FIGS. 1 and 2 are generally illustrative of such an electrosurgical device 30 for use in the treatment of esophageal obstructions whereas FIGS. 3 and 4 are generally illustrative of a similar device 32 used for the treatment of rectal obstructions or of hemorrhoids. The primary concepts of the invention, however, apply to both devices, although they differ primarily in the method of insertion of the device into a particular body cavity. At the same time, the invention is not to be limited in its application to the treatment of the interior of the body but may be used to treat external tissue as well.

For the purposes of describing the invention herein, the term "conductor" is used to describe the conductive material, such as generally covered with an electrical and thermal insulation, which carries the electrical current from its source to the electrode. The term "electrode" is used to describe the conductive material, such as generally uninsulated, which is electrically attached to the "conductor" to distribute the electrical current across the active areas of the probe. The electrode may be branched into two or more electrode strips.

It should be understood that the probes disclosed can be used with or without an endoscope. In some applications the probe can be attached to a support member and the probe located at the site of treatment without the use of an endoscope. In other applications the distal end of an endoscope can be inserted into a body cavity containing the area to be treated and the probe fed through the proximal end of the endoscope to the area to be treated. In a still further application the probe can be backloaded into the distal end of and pass through the endoscope. The distal end of the endoscope is then inserted into the body cavity to the area to be treated. In backloading the probe body is generally larger in size than the endoscope channel. The probe is mounted securely on the distal end of the endoscope before insertion into the body cavity. Thus, the proximal end of the probe shaft is passed through the distal end of the endoscope channel until only the probe body extends outside the distal end of the endoscope before the endoscope is inserted into the body cavity. Usually, the electrical leads from the power source to the probe are contained within the probe shaft before the probe is mounted onto the distal end of the endoscope and are connected to a power source at the proximal end of the endoscope after the probe shaft is fed into the endoscope.

For ease of description, the electrosurgical device 30 will first be described, then the variations which apply to the device 32.

As illustrated in FIG. 1, the electrosurgical device 30 is shown inserted into an esophagus 34 of a patient 36 for treatment of an undesired growth or tumor 38.

Figure 5:
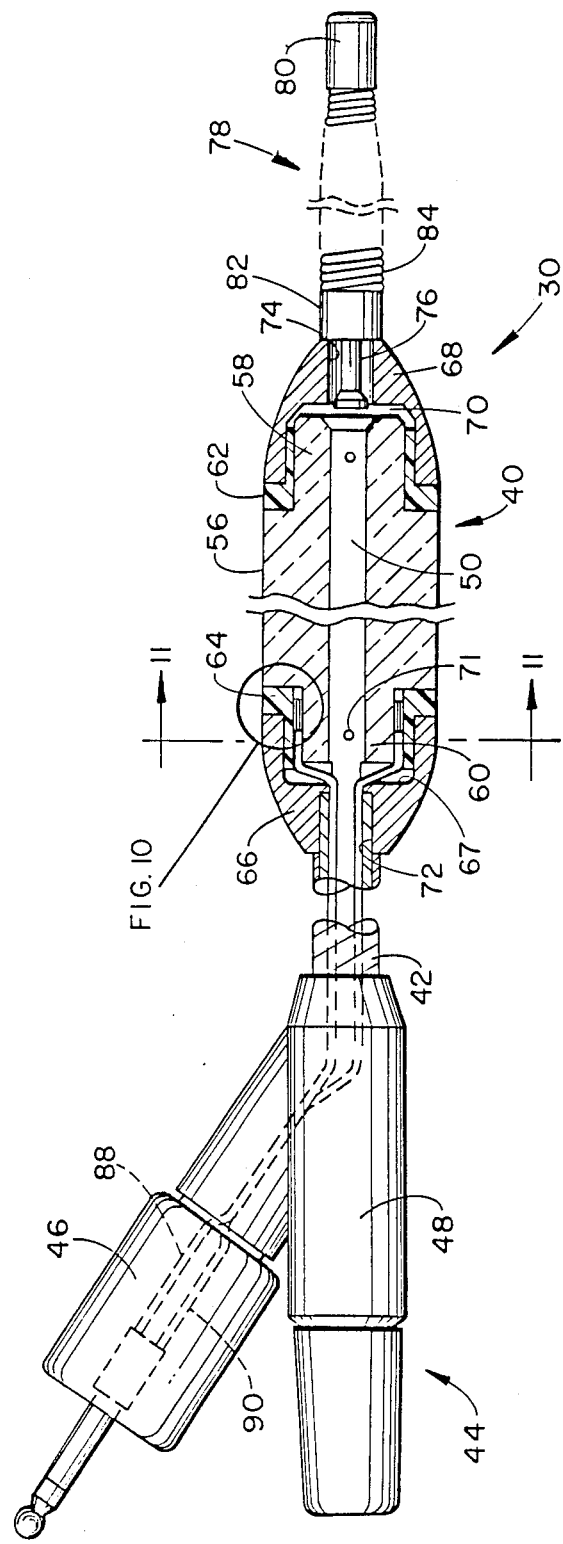
FIG. 5 is a longitudinal cross section view of the embodiment of the invention illustrated in FIGS. 1 and 2.
Figure 17:
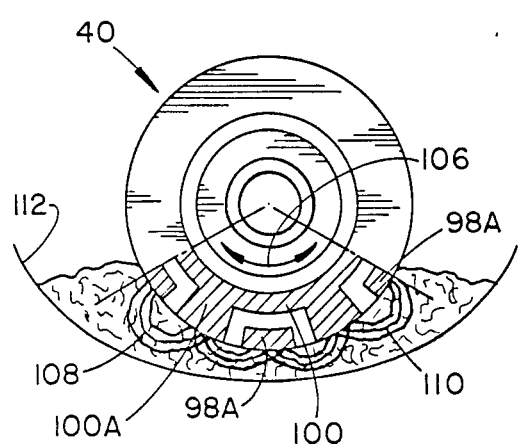
FIG. 17 is an end elevation view, broadly similar to FIG. 16, of a modified probe body in use and capable of focusing the energy it emits in a restricted arc onto only the tissue desired to be treated.

Turn now to FIG. 5 which is a substantially more detailed illustration of the electrosurgical device 30. As seen in FIG. 5, a probe body 40 at the working end of the device 30 is mounted on an extremity of a shaft assembly 42 whose other end is attached to an end assembly 44 which may include a suitable electrical connector 46 and a hollow end cap 48 which may, if desired, connect to a source of water for use as a syringe. The electrical connector 46 serves to introduce electrical energy which is to be applied to the probe body 40 in a manner to be described. The end cap 48 may also enable the insertion, through the hollow shaft assembly 42, and through a longitudinally extending and centrally disposed channel 50 in the probe body 40, of a fiber optical system for viewing the region to be treated or for reception of a flexible guide wire 52 as well as for reception of one or more tubular members for washing the site to be treated and for withdrawing waste material. The shaft assembly 42 may be of any desired length and it may be rigid or flexible as in the instance of use as depicted in FIG. 1. Additionally, as seen especially clearly in FIGS. 2 and 6, the outer surface of the assembly 42 is preferably provided with suitable circumferential markings 54A at spaced longitudinal locations to indicate the depth to which the device 30 has been inserted into a body cavity. Also, suitable longitudinal markings 54B may be provided to indicate the angular positioning of the active electrode strips of a probe body, such as shown in FIG. 17, wherein the electrode strips extend less than 360 degrees of the active member's peripheral surface. In each instance, the markings are preferably formed of colors or hues which contrast with the color or hue of the outer surface of the support member.

Turn now to FIGS. 5-12 for a more particular description of the probe body 40. The probe body 40 is substantially cylindrical in shape. In this regard, it may be in the form of a right cylinder (FIGS. 5, 7, and 8) or any other suitable shape such as olive-or barrel-shaped (FIG. 6A), that is, arcuate in a longitudinal direction. According to one operational construction, the probe body 40 may have a central member 56 and, integral therewith, a first end portion 58 and a second end portion 60. Both the first and second end portions 58, 60 have their diameters reduced from that of the central portion 56. The central member 56 and integral end portions 58, 60 are composed of ceramic material or other suitable electrically and thermally insulative substrate material.

Figure 6:
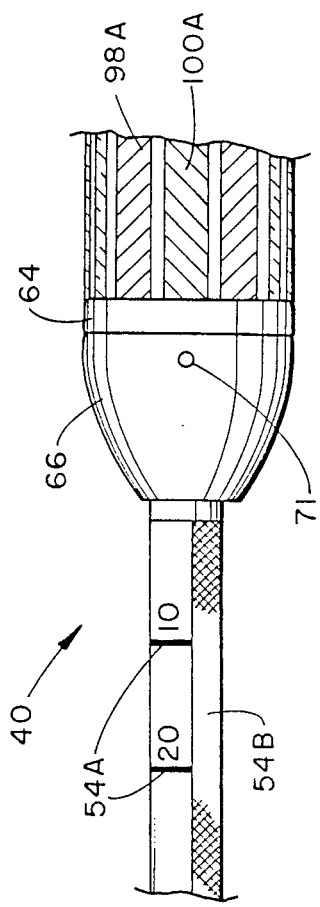
FIG. 6 is a detail side elevation view of a portion of the device illustrated in FIG. 5.

The probe body 40 illustrated in FIG. 5 is also provided with a pair of heat insulative bushings 62, 64 which are received, respectively, on the first and second end portions 58, 60. In turn, a rounded cap member 66 is provided with a recess 67 so as to be matingly received on the insulative bushing 64 and has an outer surface flared to the outer surface of the central portion 56. A suitable adhesive may be employed to fixedly join the insulative bushing 64 to the end portion 60 and, likewise, the cap member 66 to the bushing 64 (see FIG. 10). As seen in FIGS. 5 and 6, the outer diameter of the bushing 64 closely conforms to that of the central portion 56 and the flared outer contour of the cap member 66.

At the opposite end of the probe body 40, a cap member 68, somewhat similar to the cap member 66, is provided with a recess 70 so as to be matingly received on the bushing 62. As in the instance of the bushing 64 and cap member 66, the outer surfaces of the cap member 68 and bushing 62 are flared into the outer surface of the central portion 56 so as to achieve a substantially continuous unbroken surface for the entire probe body 40. Also, as at the other end of the probe body 40, a suitable adhesive may be employed to fixedly join the central member 56, first end portion 58, bushing 62, and cap member 68 together. By reason of the flared cap members 66, 68, ease of both insertion and withdrawal of the device from a body cavity can be achieved without scraping the walls of the body duct or cavity. The construction also assures a minimum of trauma and pain to the patient. The rounded shapes also provide tactile feedback to the operator or physician as to when the probe body 40 is approaching or contiguous with the constriction or tumor to be treated.

Radially extending pins 71, pre-cut to size, are received in conforming radial recesses formed in the end portion, insulative bushing, and cap member at both the proximal and distal ends of the probe body 40. With the application of suitable adhesive to the interface between the pins 71 and their associated recesses, the structure is assured to be an integral one which will not separate while in a body cavity.

It will also be appreciated that the construction illustrated in FIG. 5 is not to be limiting of the invention. For example, the end portions 58, 60 may be eliminated and the relative materials of the cap members 66, 68 and of the central portion 56 so chosen that the bushings 62 and 64 may be eliminated. Such alternative constructions are nevertheless considered to still be within the scope of the invention.

The cap member 66 is formed with a second recess 72 longitudinally spaced from the first recess 62 to matingly receive an end of the shaft assembly 42. Once again, a suitable adhesive may be employed to fixedly join the shaft assembly 42 to the cap member 66. The cap member 68 is also provided with a second recess 74, preferably tapped, so as to threadedly receive a stud 76 on a proximal end of a filliform assembly 78. The stud 76 is substantially reduced in diameter from the boss 82 and the cap member 68 is flared to the outer surface of the boss. The filliform assembly includes a smoothly contoured shaped tip end 80, a boss 82 integral with the stud 76, and a tightly coiled spring member 84 extending between and fixed at its opposite ends to the tip end 80 and the boss 82. The spring member 84 is substantially rigid in the longitudinal direction, but is transversely resilient. That is, the spring member 84 is capable of being deflected transversely when a transverse force is applied thereto at a location beyond the boss 82. The entire filliform assembly 78 is hollow and in communication with the channel 50 in the probe body 40.

The purpose of the filliform assembly 78 is to aid in the smooth and substantially trauma and pain free insertion of the electrosurgical device 30 into a convoluted body cavity such as that illustrated in FIG. 1. Thus, when the guide wire 52 has been inserted into the body cavity during a previous procedure of a known nature, in a relatively simple subsequent procedure, the device 30 can be slid onto a proximal end of the wire, then into the body cavity, following the guide wire 52 as a guide as it proceeds. By reason of its unique construction, the filliform assembly 78 can readily follow the guide wire 52 and guide the remainder of the device into a desirable position. Such a desirable position is indicated in FIG. 1 wherein the probe body 40 is positioned tangential to the tumor 38 intended to be treated.

Although a filliform assembly 78 is depicted in FIG. 5, any suitable member may be used here. For instance a cone-shaped dilator member may be used instead of the filliform. The cone-shape member, the probe body 40 to which it is attached, or alternatively of which it is an integral part, and shaft assembly 42 could all be made of a non-electrically conducting material.

As seen in FIG. 5, according to one suitable construction, a pair of electrical conductors 88, 90 extend from the connector 46, through the shaft assembly 42 and to the probe body 40. When the conductors reach the probe body 40, the conductor 88 is bent to conform closely to the end portion 60 within a groove 92 therein. The groove 92 extends first radially along a proximal end face 94 (FIGS. 8 and 9), then longitudinally along the peripheral surface of the end portion 60 generally until it reaches the central portion 56. In a similar fashion, the electrical conductor 90 is bent so as to extend along a groove 96, first radially, and then in a longitudinal direction along the peripheral surface of the end portion 60 until it generally reaches the central portion 56. Of course, it will be appreciated that the conductors 88, 90 are electrically insulated so as to be isolated from one another at all locations between the electrical connector 46 and the probe body 40.

Although the embodiment shown in FIG. 5 has shaft assembly 42, probe body 40, cap member 68 and filliform assembly 78 aligned along substantially the same longitudinal axis, this is not necessary. Other embodiments of the device which are not so aligned are considered to be part of the general disclosure herein.

Turn now to FIGS. 13–16 which generally illustrate one suitable construction of an active member of the probe body 40. As illustrated, the probe body 40 comprises the central portion 56 and end portions 58, 60 onto which electrically conductive electrode strips 98, 100 have been mounted. The electrode strips 98 and 100 are of an opposite polarity, the conductive material of strip 98 being electrically continuous with the conductor 88 and the conductive material of strip 100 being electrically continuous with the conductor 90. The conductive material may be formed of any suitable material such as gold or silver film deposited in a known manner on the surfaces of the central portion 56 and end portions 58, 60 generally as illustrated in FIGS. 13–16 and may have a film thickness, for example, of approximately one-half mil.

Figure 13:
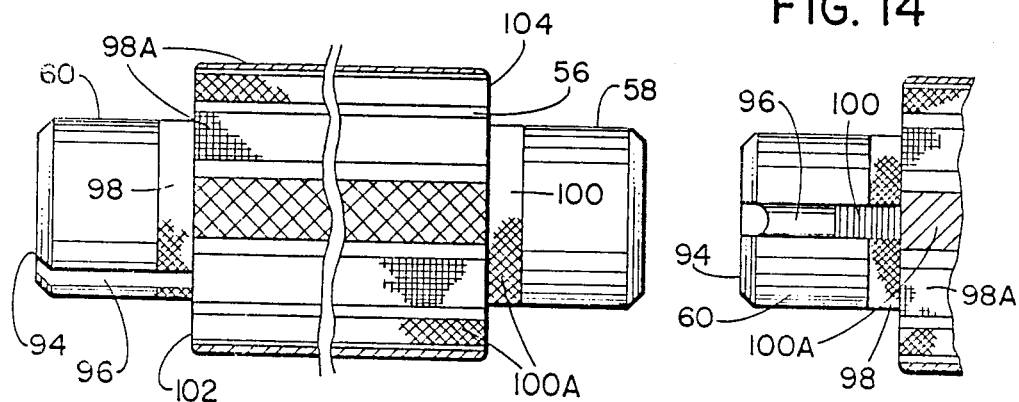
FIG. 13 is a side elevation view of the part illustrated in FIG. 8, illustrating the electrodes formed on the surfaces thereof.
Figure 14:
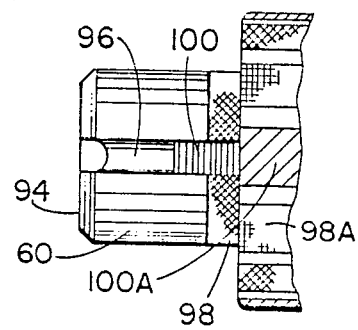
FIG. 14 is a detail side elevation view illustrating a part of structure of FIG. 13 from another vantage point.
Figure 15:
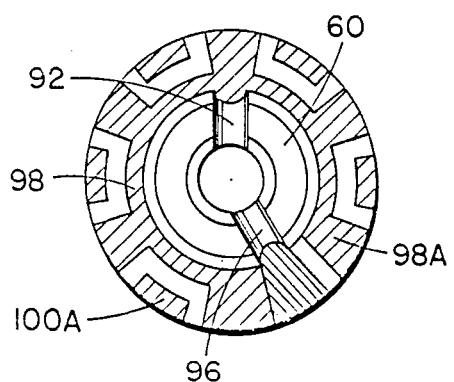
FIG. 15 is an end elevation view of the structure illustrated in FIG. 13 taken from the left hand end thereof.
Figure 16:
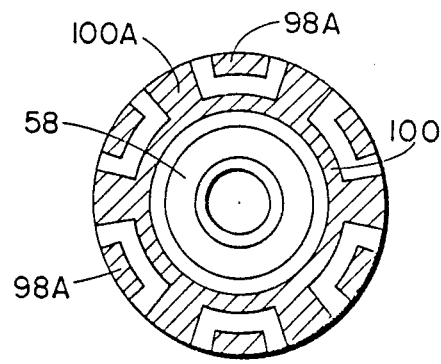
FIG. 16 is an end elevation view of the structure illustrated in FIG. 13 taken from the right hand end thereof.

Specifically, viewing FIGS. 13 and 15, a ring of the conductive material 98 is formed concentric with the central portion 56 on one end wall 102 thereof and, at spaced radial locations, extends radially outwardly toward, then onto and across, an outer surface of the central portion 56 in a longitudinal direction. The conductive material 98 also extends a short distance on the outer peripheral surface of the end portion 60 in the direction of the end face 94. The conductive material 98 also covers a portion of the length of the groove 96 so as to establish electrical continuity with the electrical conductor 88.

In a similar fashion, the conductive material 100 is formed as a ring concentric with the central portion 56 on a distal end wall 104 of the central portion 56. The conductive material 100, then, at spaced radial locations extends outwardly toward, then onto the peripheral surface of the central portion 56 and extends longitudinally thereacross to the opposite end face 102. Also, the bottom of the groove 96 is coated with the conductive material 100 to assure electrical continuity thereof with the conductor 90. It will be seen that individual electrode strips 98A correlating with the electrode material 98 may be generally of uniform width and associated uniform spacing and may be interposed with electrode strips 100A correlating with the electrode material 100. The ratio of the width of the electrodes to the spacing between adjacent electrodes is so selected as to enable effective bipolar treatment of tissue.

In the alternative, the width of an individual electrode strip, and the associated spacing(s) from its adjacent electrode, need not be uniform but may vary depending on the specific application.

As seen in FIG. 2, electrosurgical devices 30 are illustrated in a series of graduated sizes of probe bodies 40, both in terms of outer diameter and in terms of the effective length of the central portion 56 on which the electrode strips 98A and 100A are positioned. By choosing a probe body with a specific length of central portion 56, a more focused treatment can be achieved. This ability is particularly helpful when treating smaller obstructions or tumors.

More precise focusing can also be achieved by means of the construction illustrated in FIG. 17. In this instance, electrode strips 98A and 100A are mounted on the outer peripheral surface of the probe body 40, and specifically the central portion 56, so as to cover only that part of the peripheral surface positioned within a defined arc 106 having as its center the longitudinal axis of the probe body. The electrode strips 98A are illustrated as being of uniform width and spacing although those electrode strips 98A which are at the outermost locations of the arc may have approximately half the width of the remaining electrode strips since their influence, as schematically represented by electrical flux lines 108, is in the direction of their only neighboring electrode strip. As seen in FIG. 17, the probe body 40 is effective to direct its flux in a focused fashion against only the obstructions 110 extending into a body cavity 112 and not at adjacent locations 114 of healthy tissue which might otherwise be harmed with an unfocussed system.

Figure 6A:
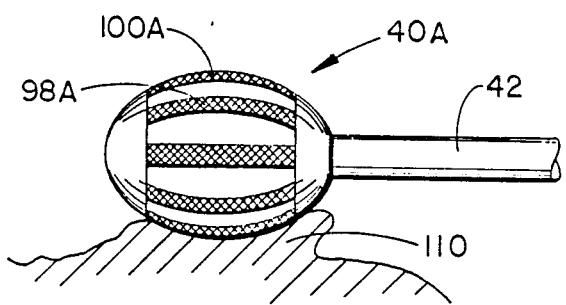
FIGS. 6A and 6B are a detail side elevation views of a modified construction of the device illustrated in FIG. 5.

It was previously mentioned that the probe body 40 is substantially cylindrical and such a description is to be taken as being sufficiently broad to include the barrel-shaped probe body 40A in which the outer surface is arcuate in a longitudinal direction as seen in FIG. 6A. Such a design enables, in some instances, a deeper, better focused, and more uniform electrical flux penetration of the obstruction.

Figure 18:
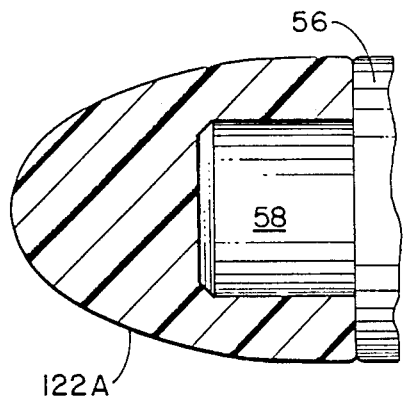
FIG. 18 is a detail cross section view illustrating a modified portion of a probe body according to the invention.

Another embodiment of the invention has previously been mentioned with respect to FIGS. 3 and 4. This embodiment provides a probe body 120 which is generally similar to the probe body 40 with the exception of a distal cap member 122. In this instance, the cap member 122 serves as an extreme end of the probe body, being absent the filliform assembly 78 of the preceding embodiment. The cap member 122 may have an aperture therethrough such as the recess 74 in the cap 68 for the purposes previously recited, or it may be provided without an aperture (FIG. 18). As seen in Fig. 18, the cap member is composed of solid, substantially rigid plastic material, suitably attached to the central member 56. In any event, the cap member 122 is flared into the remaining surfaces of the probe body 120 to assure ease of, and painless, insertion of the probe member into a body cavity. In a similar fashion, the cap member 66 may also be flared into the remainder of the probe body for the same purposes upon withdrawal of the probe body from the body cavity. Of course, it will be appreciated that no flaring is necessary in the event the probe body 120 has substantially the same diameter as a support shaft 124.

With particular attention to the illustration in Fig. 4, the probe body 120 is shown mounted to the end of the shaft 124 which, in this instance, may be of a substantially rigid construction. An analoscope 126 is depicted as being inserted into the anal cavity 128. The analoscope serves to guide, and thereby eases, the insertion of the probe body 120 therein for the treatment of obstructions 130 which may be in the form of undesirable growths or hemorrhoids.

Turn now to FIGS. 19-26 which are illustrative of one suitable form of a handle member 136 which is usable with any of the constructions previously described but is particularly applicable to the embodiments of FIGS. 3, 4, and 17. In a manner about to be described, the handle member 136 serves to support the probe body for rotation about its longitudinal axis. Such a movement is particularly desirable when using the focused electrode construction illustrated in FIG. 17.

The handle member 136 includes a grip 138 and an integral cap assembly receiving portion 140 having an elongated bore 142 therethrough and an elongated slot 144 parallel to and in communication with the bore along its length. The slot 144 is sized to freely receive the shaft 124 therein, but has a width substantially less than the diameter of the bore. An actuating mechanism which is operably associated with the handle member 136 is illustrated in FIGS. 19, and 23-26. The actuating mechanism includes a sleeve 146 (FIGS. 23 and 24) slidably receivable in the bore 142 and a locking collar 148 (FIGS. 25 and 26). A radially extending circumferential flange 150 is integral with the sleeve 146 at one end thereof and has a knurled outer peripheral surface 152 defining a thumbwheel. Adjacent to but spaced from the end which is opposite the radial flange 150, the sleeve is provided with an annular groove 154. As best illustrated in FIGS. 3 and 19, the sleeve 146 is slidably inserted into the bore 142 of the handle member 136. Thereupon, the locking collar 148 which may be formed of a somewhat flexible material, "DELRIN" brand plastic being a suitable choice for purposes of the invention, is then slid onto that end of the sleeve 146 opposite the flange 150 until a circular flange 156 (FIG. 26) on the collar 148 is received and locks in place in the annular groove 154. When this occurs, the sleeve 146 is held firmly in place on the handle member 136 against substantially all movement except for rotation thereon.

The locking collar 148 has an eccentric opening 158 and a slot 160 similar in width to the slot 144. In a similar fashion, the sleeve 146 has a passageway 162 having a diameter generally similar to that of the eccentric opening 158 and itself has a slot 164 aligned with passageway 162 and having an opening generally at the same size as that of the slots 160 and 144. The flange 150 is also formed with a funnel shaped slot 166 generally aligned with the slot 164 which serves as a locking expedient to axially secure the shaft 124 as seen in FIG. 19.

Thus, when it is desired to attach the handle member 136 onto the shaft 124, the slot 160 of the locking collar 148 is aligned with the slots 144, 164, and 166 to thereby laterally receive the shaft therein. Of course, it would also be possible, and perhaps desirable, to backload the shaft 124 into the handle member 136, that is, longitudinally insert the shaft from its rear, or connection end, through the passageway 162. When the shaft achieves a desired position within the passageway 162 and eccentric opening 158, the locking collar 148 is then rotated so that the eccentric opening creates a locking interference on the shaft 124 between opening 158 and passageway 162. In this fashion, the shaft 124 is locked onto the handle member 136 and is not removable therefrom until the locking collar 148 is returned to its original unlocked orientation. The funnel shaped slot 166 is preferably slightly smaller than the outer diameter of the shaft 124 so that it snugly engages the shaft. As with the locking collar 148, the sleeve 146 may be formed of a suitable moderately flexible material such as "DELRIN" brand plastic.

Thus, when the operator turns the thumbwheel 152 while holding the grip 138, the shaft 124 is rotated about its longitudinal axis with the result that the probe body 120 can be angularly positioned to accurately focus on the obstruction to be treated. The outer surface of the shaft 124 may rotationally frictionally engage (such as by a detent mechanism, ratchet mechanism, adjustable friction screw mechanism or other suitable device) the opening 158 of the collar 148 so as to cause sufficient drag to maintain the rotational position of the shaft when movement caused by the thumbwheel 152 ceases. Of course, other expedients may be employed for the same end result.

A further feature of the handle member 136 resides in the placement of a suitable indicator, such as an electrical lamp 168, which is suitably connected to the electrical circuitry previously described for energizing the probe body 120 to indicate to the operator when electrical current is flowing. Also, a spring loaded trigger 170 may be employed by the operator to selectively energize the probe body 120.

Figure 6B:
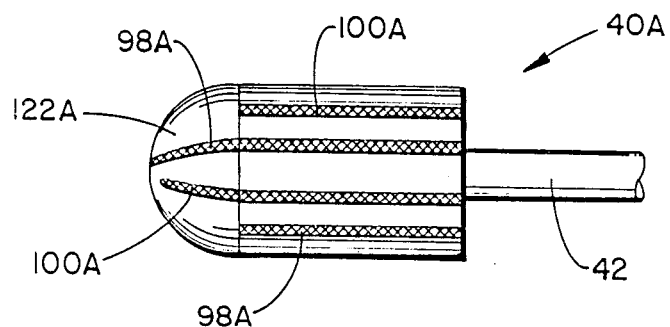
Figure 7:
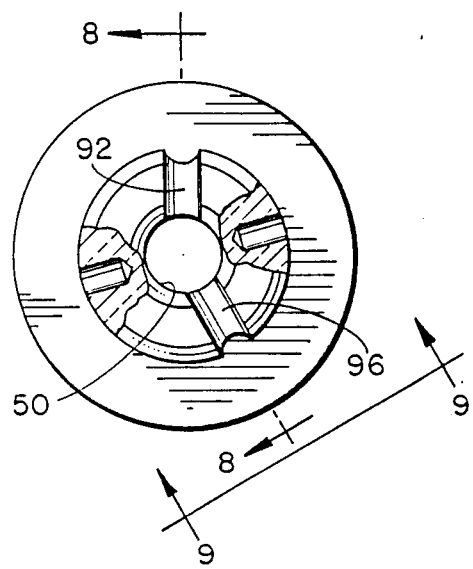
FIG. 7 is an end elevation view of a component of the invention illustrated in FIG. 5; certain parts being cut away and shown in section.
Figure 9:
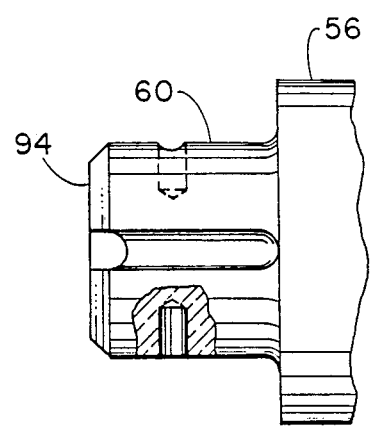
FIG. 9 is a detail side elevation view of a portion of the structure illustrated in FIG. 8, certain parts being cut away and shown in section.
Figure 8:
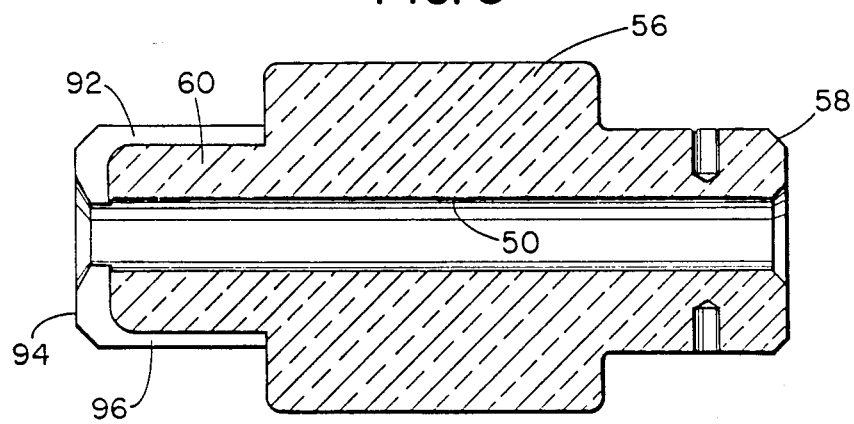
FIG. 8 is a cross section view taken generally along line 8—8 in FIG. 7.
Figure 10:
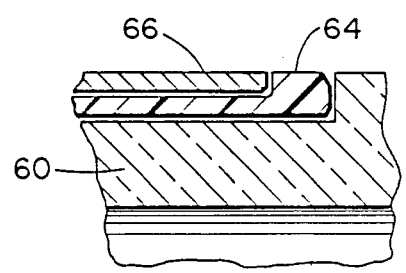
FIG. 10 is an enlarged detail view of a portion of FIG. 5.
Figure 11:
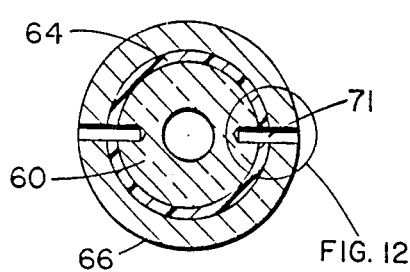
FIG. 11 is a cross section view taken generally along line 11—11 in FIG. 5.
Figure 12:
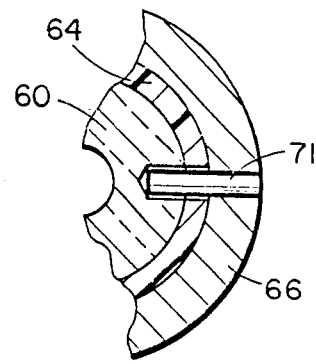
FIG. 12 is an enlarged detail cross section view of a portion of FIG. 11.

A further alternative embodiment of the probe is shown in FIG. 6B. Here, the probe body 40A may be cylindrical in shape and contain a first electrode with two branch electrode strips 98A and a second electrode with two branched electrode strips 100A of opposite polarity interleaved therebetween. Here it can be seen that the electrode strips occupy only a small portion of the peripheral surface of the active area of the probe (approx. 90 degrees) thereby making the probe of the focussed type. In addition it is seen that one pair of electrode strips, 98A and 100A, extend over cap 122A. It is to be understood that more than two strips may extend over the cap in this type of focussed probe.

It has been found to be advantageous when using the focussed probe to use a scheme by which the electrodes are visually contrasted against the substrate of the active area of the probe. For example, in the focussed probe body 40 A shown in FIG. 17, the color or hues of the electrodes 98A, 100 A may preferably be selected to contrast with the color or hues of the outer surface of their support member, in the case probe body 40A. In this manner, the operator of the probe can visually determine, either through the direct observation or observation through an optical system such as a fiber optics bundle, if the electrodes of the focussed probe are precisely located for treatment since the position of the electrodes will be easily detected. Other means beyond contrasting colors and hues may be used to create the contrast such as different surface textures, different surface patterns, etc.

While preferred embodiment of the invention have been disclosed in detail, it should be understood by those skilled in the art that various modifications may be made to the illustrated embodiments without departing from the scope described in the specification and defined in the appended claims.

What is claimed is:

1. An electrosurgical device for use in the treatment of tissue comprising:
    a probe body including:
    an active member sufficiently energized to cauterize and/or dessicate tissue and/or coagulate blood having a peripheral surface extending between first and second ends and at least a pair of spaced, longitudinally extending, electrodes on said surface connected, respectively, to opposite poles of an alternating current source of electrical energy, said electrodes defining a limited active area for focusing its energy on only a restricted region of tissue adjacent thereto desired to be treated while leaving other regions of tissue unaffected, said electrodes being of suitable width and spacing for bipolar treatment and being mounted on said peripheral surface so as to cover only that part of said peripheral surface positioned within a defined arc of less than 360° having as its center the longitudinal axis of said active member; and
    a non-active member having a contoured peripheral surface adjacent said active member 2. An electrosurgical device as set forth in claim 1 wherein there are at least two pairs of said electrodes and wherein said electrodes are of uniform width and spacing and are of a predetermined length in order to assure a desired degree of focus of treatment in the longitudinal direction.

3. An electrosurgical device as set forth in claim 1 wherein there are at least two pairs of said electrodes and wherein said electrodes are of any suitable width and spacing and are of a predetermined length in order to assure a desired degree of focus of treatment in the longitudinal direction.

4. An electrosurgical device as set forth in claim 3
    wherein said electrodes that are at the outermost locations of the arc on said peripheral surface have generally half the width of said remaining electrodes.

5. An electrosurgical device as set forth in claim 4 wherein said active member is substantially cylindrical.

6. An electrosurgical device as set forth in claim 5 wherein said peripheral surface is arcuate in a longitudinal direction.

7. An electrosurgical device as set forth in claim 1 wherein said active member is substantially cylindrical.

8. An electrosurgical device as set forth in claim 1 wherein said contoured peripheral surface of said non-active member is arcuate in a longitudinal direction.

9. A probe body as set forth in claim 1 including:
    a filliform assembly mounted on said non-active member coaxial with said active member and extending in a direction away therefrom, said filliform assembly including a smoothly contoured cylindrically shaped tip end having a diameter substantially less than that of said central portion; and
    a tightly coiled spring member extending between and fixed at its opposite ends to said non-active member and to said tip end, said spring member being substantially rigid in the longitudinal direction, but being transversely resilient.

10. An electrosurgical device as set forth in claim 1 including:
    a handle member mounted to said elongated support member; and
    actuating means operatively associated with said handle member and engaged with said support member when said handle member is mounted thereon for rotating said support member about a longitudinal axis thereof while said handle member remains stationary.

11. An electrosurgical device as set forth in claim 10 wherein said handle is releasably mounted to said elongated support member.

12. An electrosurgical device as set forth in claim 11: wherein said support member is a shaft assembly; and wherein said handle member includes a grip portion.

13. An electrosurgical device as set forth in claim 10 including:
    indicator means on said handle member for indicating when said electrodes are being energized.

14. An electrosurgical device as set forth in claim 13 wherein said indicator means is an electric lamp.

15. An electrosurgical device as set forth in claim 10 wherein said handle is releasably mounted to said elongated support member.

16. An electrosurgical device as set forth in claim 1 including:
    a handle member mounted to said elongated support member; and
    actuating means operatively associated with said handle member and engaged with said support member when said handle member is mounted thereon for actuating said support member while said handle member remains stationary.

17. An electrosurgical device as set forth in claim 1 including:
    a handle member mounted to said elongated support member; and
    rotational means operatively associated with said handle member for rotating said support member about a longitudinal axis thereof while said handle member remains stationary.

18. An electrosurgical device as set forth in claim 1, wherein said contoured surface is so shaped that it provides tactile feedback to the operator as to when the probe body is approaching or contiguous with the area to be treated.

19. An electrosurgical device as set forth in claim 1 wherein said support member has a longitudinal axis and wherein said probe body is receivable into a body cavity for movement both along the longitudinal axis and rotationally about the longitudinal axis, said support member having first markings thereon for indicating the depth of said probe body within the body cavity and/or second markings thereon for indicating the rotational position of said probe body within the body cavity.

20. An electrosurgical device as set forth in claim 19 wherein said first markings are located at substantially uniform increments along said support member and wherein said second markings are located at substantially uniform increments extending longitudinally of said support member.

21. An electrosurgical device as set forth in claim 20 wherein said first and second markings are formed of colors which contrast with the outer surface of said probe body.

22. The electrosurgical device as in claim 1 wherein there is a contrast means provided between the peripheral surface of said probe body and said electrodes.

23. The electrosurgical device as in claim 22 wherein said contrast means is provided by said probe body being of a first color and said electrodes being of a second color which contrasts with said first color.

24. An electrosurgical device as set forth in claim 1 wherein said probe body is available in a plurality of shapes and sizes, each adapted for treating a specifically shaped and sized region of tissue; and including:
a handle member for releasably mounting thereon said support member associated with a specific shape and size of said probe body to be selected for tissue treatment.

25. An electrosurgical device as set forth in claim 1 including:
an elongated support member fixed to said second end of said active member and extending in a direction away therefrom.

26. An electrosurgical device as set forth in claim 1 wherein said contoured peripheral surface of said non-active member is an extreme end of said probe body.

27. An electrosurgical device for use in the treatment of tissue comprising:
a multipolar probe body sized to enable passage of said probe body into and within a body cavity whose tissue is to be treated;
said probe body having a first end and a second end and including:
an active member sufficiently energized to cauterize and/or dessicate tissue and/or coagulate blood for providing focussed treatment of tissue having a peripheral surface and a longitudinal axis extending between said first end and said second end, said active member having an energized region on said peripheral surface positioned within a defined arc of less than 360° having as its center the longitudinal axis of said active member, said energized region defining a limited active area for focusing energy on only a restricted region of tissue adjacent thereto desired to be treated while leaving other regions of tissue unaffected; and
a non-active member having a rounded peripheral surface at said second end of said probe body, said rounded surface being an extreme end of said probe body.

28. An electrosurgical device as set forth in claim 27 wherein said active member includes:
at least two electrically isolated electrodes mounted on said peripheral surface, each of said electrodes including a conductor for connecting said electrodes to a source of electrical energy.

29. The electrosurgical device as in claim 28 wherein there is a contrast means provided between the peripheral surface of said active member and said electrodes.

30. The electrosurgical device as in claim 29 wherein said contrast means is provided by said peripheral surface being of a first color and said electrodes being of a second color which contrasts with said first color.

31. An electrosurgical device as set forth in claim 27 wherein said active member includes:
at least first and second electrically isolated conductors mounted on said peripheral surface including means for connecting said conductors to a source of electrical energy, each of said conductors comprising at least two electrodes with said electrodes of said first conductor being separated from and interposed with said electrodes of said second conductor with a spacing therebetween, said electrodes being so distributed and respectively so sized in width and length as to extend in spaced apart relationship to respective locations at said first end spaced from said support member and at said second end spaced from said non-active member, the ratio of the width of said electrodes to the spacing between said adjacent electrodes being so selected as to enable effective bipolar treatment of tissue with effectively omnidirectional probe body orientations relative to the tissue to be treated.

32. An electrosurgical device as set forth in claim 27 including:
a plurality of pairs of first and second electrically isolated electrodes mounted on said perpheral surface of said active member, each of said electrodes including a conductor for connection to a source of electrical energy, said first electrodes being of an opposite polarity from said second electrodes, said electrodes being of suitable width and spacing for effective bipolar treatment and of a predetermined length to assure a desired degree of focus of treatment in the longitudinal direction.

33. An electrosurgical device for use in the treatment of tissue comprising:
a probe including:
a body member having a peripheral surface extending between first and second ends and at least a pair of spaced, longitudinally extending, electrodes on said surface connected, respectively, to opposite poles of a source of electrical energy;
a cap member having a contoured peripheral surface mounted to said first end of said active member, said contoured surface being an extreme end of said probe body;
said device including an elongated support member fixed to said second end of said body member and extending in a direction away therefrom wherein said electrodes are of suitable width and spacing to provide effective bipolar treatment and are mounted on said peripheral surface so as to cover only that part of said peripheral surface positioned within a defined arc of less than 360° having as its center the longitudinal axis of said body members, whereby the energy being emitted from said electrodes can be focussed on a restricted area selected for treatment, and
at least a pair of said electrodes extending from the body onto said cap member.

34. The electrosurgical device as in claim 33 wherein the body member has a pair of electrodes each of which has at least two electrode strip branches and less than all electrode strip branches extend onto the partially cap area.

* * * * *